(12) United States Patent
Doney et al.

(10) Patent No.: US 7,943,165 B2
(45) Date of Patent: May 17, 2011

(54) SALINE NOSE WIPE AND METHODS OF MANUFACTURE AND USE

(75) Inventors: Mindee K. Doney, Beaverton, OR (US); Julienne M. Pickens, Tigard, OR (US)

(73) Assignee: Little Busy Bodies, Inc., Beaverton, OR (US)

( * ) Notice: Subject to any disclaimer, the term of this patent is extended or adjusted under 35 U.S.C. 154(b) by 52 days.

(21) Appl. No.: 12/228,426

(22) Filed: Aug. 11, 2008

(65) Prior Publication Data

US 2009/0087465 A1  Apr. 2, 2009

Related U.S. Application Data

(60) Provisional application No. 60/964,327, filed on Aug. 10, 2007.

(51) Int. Cl.
*A61K 9/70* (2006.01)

(52) U.S. Cl. ........ 424/443; 424/744; 424/764; 424/679; 424/680

(58) Field of Classification Search .................. None
See application file for complete search history.

(56) References Cited

U.S. PATENT DOCUMENTS

| | | | |
|---|---|---|---|
| 5,049,440 A | 9/1991 | Bornhoeft | |
| 5,453,445 A * | 9/1995 | Henry | 514/626 |
| 5,770,183 A * | 6/1998 | Linares | 424/59 |
| 6,361,784 B1 * | 3/2002 | Brennan et al. | 424/402 |
| 6,429,261 B1 | 8/2002 | Lang et al. | |
| 6,444,214 B1 | 9/2002 | Cole et al. | |
| 6,548,592 B1 | 4/2003 | Lang et al. | |
| 6,579,570 B1 | 6/2003 | Lang et al. | |
| 6,599,848 B1 | 7/2003 | Chen et al. | |
| 6,602,955 B2 | 8/2003 | Soerens et al. | |
| 6,649,262 B2 | 11/2003 | Hoo et al. | |
| 6,651,924 B2 | 11/2003 | Gingras et al. | |
| 6,653,406 B1 | 11/2003 | Soerens et al. | |
| 6,683,143 B1 | 1/2004 | Mumick et al. | |
| 6,713,414 B1 | 3/2004 | Pomplun et al. | |
| 6,727,196 B2 | 4/2004 | Yahiaoui et al. | |
| 6,811,638 B2 | 11/2004 | Close et al. | |
| 6,814,974 B2 | 11/2004 | Cole et al. | |
| 6,815,502 B1 | 11/2004 | Lang et al. | |
| 6,828,014 B2 | 12/2004 | Branham et al. | |
| 6,835,678 B2 | 12/2004 | Jackson et al. | |
| 6,897,168 B2 | 5/2005 | Branham et al. | |
| 6,908,966 B2 | 6/2005 | Chang et al. | |
| 6,946,413 B2 | 9/2005 | Lange et al. | |
| 6,994,865 B2 | 2/2006 | Branham et al. | |
| 7,070,854 B2 | 7/2006 | Chang et al. | |
| 7,101,456 B2 | 9/2006 | Bunyard et al. | |
| 7,101,587 B2 | 9/2006 | Gingras et al. | |
| 7,101,612 B2 | 9/2006 | Lang et al. | |
| 7,141,519 B2 | 11/2006 | Bunyard et al. | |
| 7,157,389 B2 | 1/2007 | Branham et al. | |
| 7,176,150 B2 | 2/2007 | Kopacz | |
| 7,179,502 B2 | 2/2007 | Hoo et al. | |
| 7,235,250 B2 | 6/2007 | Padlo et al. | |
| 7,276,459 B1 | 10/2007 | Lang et al. | |
| 7,456,117 B2 | 11/2008 | Branham et al. | |
| 7,772,138 B2 | 8/2010 | Lostocco et al. | |
| 7,772,445 B2 | 8/2010 | Chen et al. | |
| 2006/0147505 A1 * | 7/2006 | Tanzer et al. | 424/443 |
| 2008/0138383 A1 * | 6/2008 | Bortz et al. | 424/434 |

* cited by examiner

*Primary Examiner* — Susan Hoffman

(74) *Attorney, Agent, or Firm* — Marger, Johnson & McCollom, P.C.

(57) ABSTRACT

The present invention generally relates to a wet wipe or sheet that is suitable for contacting the skin and removing mucus from the skin. More specifically, the present invention relates to a wet wipe having an aqueous saline component suitable for dissolving and removing mucus in combination with the fabric matrix of the wet wipe. Typically, the fabric matrix of the wet wipe has a capacity of about 125 grams of solution per square meter, and it is impregnated with the aqueous saline solution to a level at or below approximately 80% of the absorbent capacity of the matrix.

14 Claims, 1 Drawing Sheet

SALINE NOSE WIPE AND METHODS OF MANUFACTURE AND USE

CROSS-REFERENCE TO RELATED APPLICATION

This application claims priority under 35 U.S.C. 119(e) to U.S. Provisional Patent Application No. 60/964,327 entitled "Saline Nose Wipe," filed Aug. 10, 2007, the disclosure of which is incorporated herein by reference.

BACKGROUND

Personal hygiene products such as wet wipes can have many applications. They may be used to clean up small children and infants for example, wiping a baby's bottom when changing a diaper. Wipes may be used for cleaning hands, or as a bath tissue. Wipes may also be used by a caregiver to clean an individual for whom they are providing care. Finally, wet wipes may be used in and for a number of other applications where the wetness or moisture of the wipe or towel gives some benefit.

People of all ages use personal hygiene cloths and papers to clean various areas of the body. A dry tissue is typically used to clean a wet area. For example, dry tissues are used to wipe the nose. However, it may be difficult to fully remove mucus, especially dried-on mucus, using a dry tissue. Even using a tissue having added moisturizer, a dry tissue quickly becomes irritating to the skin, particularly for infants and children. In a typical application of prior art saline treatments, a parent or other caregiver applies saline liquid to a child's nose, waits some length of time for the saline to work on the mucus, and then attempts to wipe the child's face with a dry Kleenex™ or cloth, or have the child blow his or her nose into the Kleenex™ or cloth.

It is often difficult to use nasal sprays or other mucus treatment products in this way with children, or to repeatedly wipe the child's face clean, without irritating the child's skin, particularly since children may not hold still during cleaning. Traditional methods of using saline to address mucus problems, as noted above, are therefore problematic in that it is generally uncomfortable, especially for children, to drop or spray saline into the nasal cavity.

It is therefore desirable to more easily remove mucus from children's noses, hands, and faces in a manner that is gentle and quick.

Personal hygiene wipes and associated products are found in U.S. Pat. Nos. 4,576,728, 4,772,501, 5,215,759, 5,353,485, 5,599,335, 5,669,894, 6,017,833, 6,361,784, 6,412,656, 6,579,391, 7,059,493, and 7,101,612, and U.S. Patent Application Publication No. 2007/0000064, the disclosures of which are incorporated herein by reference.

SUMMARY

The present disclosure relates generally to a matrix or sheet impregnated with an aqueous solution for use in maintaining personal hygiene. More specifically, it relates to a biologically compatible saline impregnated wipe for removal of mucus, such as from a child's nose or face.

In one embodiment, the biologically compatible matrix includes an absorbent matrix that supports an aqueous cleaning solution. The solution, in turn, may include a combination of an inorganic salt, an emollient, a preservative, and a surfactant.

The inorganic salt of the cleaning item may include sodium chloride or potassium chloride, or another appropriate inorganic salt. When present, the inorganic salt may be included at a concentration of approximately 0.1 to 9 grams per 100 grams of aqueous solution.

The emollient of the cleaning item may include glycerin, or another appropriate skin-treatment ingredient. Glycerin may also perform a solvent role in the disclosed cleaning solution and other appropriate solvents may include, for example, 1,3 propanediol, butylene glycol, or alcohol, among others.

When included, the preservative may include a chelating agent, such as: tetrasodium ethylenediamine tetraacetic acid (EDTA), disodium EDTA, trisodium EDTA, or dipotassium EDTA.

An appropriate surfactant may include disodium cocoamphodiacetate.

In some instances, the biologically compatible cleaning item may further include a cosmetic additive, like aloe vera, lavender, chamomile, or another appropriate additive. The cleaning item may also further include a buffering agent such as disodium phosphate.

A matrix used in the disclosed embodiments preferably has an absorbent capacity of approximately 1 to 5 grams of cleaning solution per 1 gram of matrix, with the solution being impregnated into the matrix at a level of less than approximately 80 percent of the absorbent capacity of the matrix. In some embodiments, the absorbent matrix is a fabric having a basis weight of approximately 10 to 100 grams per square meter, and the fabric may be organic (such as cotton) or synthetic (such as polyester or nylon). The fabric base may be woven or it may be nonwoven, such as being spunlace or layered and cross-linked.

In another embodiment, a biologically compatible cleaning system may include both an absorbent fabric base supporting an aqueous cleaning solution and a container having a storage compartment for storing at least the matrix. In embodiments having a container, the container may be compartmentalized, having two or more storage compartments, such that a first compartment may store the absorbent fabric base with included cleaning solution and a second compartment may store a dry component. In other embodiments of a system having a container the first compartment may store the absorbent fabric base and a second compartment may store the aqueous cleaning solution. In this embodiment, the solution may be applied to the fabric base shortly prior to its use in a cleaning process.

An exemplary embodiment of an absorbent fabric base used in this cleaning system, or with the cleaning solution in general, may be one that supports about 125 grams of the cleaning solution per square meter of the fabric, whether the solution is impregnated, absorbed into the fabric, or otherwise held in or to the matrix of the fabric. In a typical embodiment of a fabric base used with a container, the base may be approximately 0.04 square meters in area (or about the size of a 7 inch-by-7 inch square).

As with the first embodiment of the cleaning item, a cleaning item used in the system may include a cleaning solution with sodium chloride or potassium chloride, or another appropriate inorganic salt. When present, the inorganic salt may be included at a concentration of approximately 0.1 to 9 grams per 100 grams of aqueous solution. The cleaning item's solution may also include an emollient, a preservative, and/or a surfactant as above. In this embodiment, and the others, the cleaning solution of the system or the item itself may further include a fragrance additive, an herbal additive, or another additive that is compatible with the base ingredients of the cleaning solution.

One exemplary embodiment of a use of the described absorbent matrix material may be in cleaning mucus, dirt, or other debris from a person's skin, especially cleaning mucus from around a child's facial area. A user of a matrix material supporting a biologically compatible aqueous cleaning solution may wipe a person's skin, perhaps their own, with the absorbent matrix material. In this case, as with the others, the cleaning solution may include an inorganic salt, an emollient, and a surfactant.

As noted, the biologically compatible cleaning item is based on an absorbent matrix. Generally, the matrix has an absorbent capacity of approximately 1 to 5 grams of cleaning solution per 1 gram of matrix (or about 125 grams of solution per square meter of the matrix), and the solution is impregnated into the matrix at a level of less than approximately 80 percent of the absorbent capacity of the matrix. In some embodiments, the absorbent matrix is a fabric having a basis weight of approximately 10 to 100 grams per square meter, and the fabric may be organic (such as cotton) or synthetic (such as polyester or nylon). The fabric base may be woven or it may be nonwoven, such as being spunlace or layered and cross-linked.

In some embodiments, where the matrix and cleaning solution are provided in a storage container, the user may first remove the absorbent matrix from the container. If the container is a single-use container, or a multi-use container storing a number of wetted matrices in a distinct compartment, the user may wipe the mucus immediately upon removing the wipe from the storage container. If the container is a multi-use container having dry fabric matrix stored separately from the cleaning solution, the user may first wet the matrix with either a pre-measured or desired amount of the cleaning solution before applying it to clean away mucus, dirt, or other debris from a person's skin.

In this and other embodiments, the cleaning solution may include aloe vera, lavender, chamomile, or any other additive that may provide a desired healthful effect. An example of another additive of this type is a vitamin, or a mineral.

Another embodiment provides a method of manufacturing a biologically compatible cleaning item. The method may include the steps of providing an absorbent matrix for a biologically compatible cleaning solution, and impregnating the cleaning solution into the matrix. The matrix may have an absorbent capacity of approximately 1 to 5 grams of aqueous solution per 1 gram of matrix, and the cleaning solution may include an inorganic salt (in a concentration of 0.1 to 9 grams per 100 grams of solution), a preservative, and an emollient. The solution may be impregnated into the matrix in an amount less than approximately 80 percent of the absorbent capacity of the matrix.

As noted, the biologically compatible cleaning item is based on an absorbent matrix with an absorbent capacity of approximately 1 to 5 grams of cleaning solution per 1 gram of matrix, and the solution is impregnated into the matrix at a level of less than approximately 80 percent of the absorbent capacity of the matrix. In some embodiments, the absorbent matrix is a fabric having a basis weight of approximately 10 to 100 grams per square meter, and the fabric may be organic (such as cotton) or synthetic (such as polyester or nylon). The fabric base may be woven or it may be nonwoven, such as being spunlace or layered and cross-linked.

The inorganic salt of the cleaning item may include sodium chloride or potassium chloride, or another appropriate inorganic salt. When present, the inorganic salt may be included at a concentration of approximately 0.1 to 9 grams per 100 grams of aqueous solution. The emollient of the cleaning item may include glycerin, or another appropriate skin-treatment ingredient. When included, the preservative may include a chelating agent, such as: tetrasodium ethylenediamine tetraacetic acid (EDTA), disodium EDTA, trisodium EDTA, or dipotassium EDTA. An appropriate surfactant may include disodium cocoamphodiacetate.

DETAILED DESCRIPTION

Figure 1:
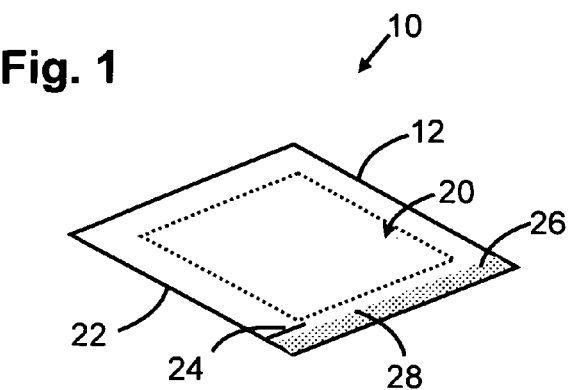
FIG. 1 is an embodiment of a container for use with a disclosed hydrated sheet.

The present disclosure describes a biologically compatible cleaning solution for removing mucus. The solution is impregnated into, or otherwise supported on, an absorbent matrix or substrate. The term "biologically compatible" means that the cleaning solution will not cause injury, toxic or immunologic reaction to living tissue; i.e. the product is well-tolerated by the body without a general fear of its inducing any adverse reactions. The term "impregnated" simply means that the solution is held within the voids present in the matrix. In some embodiments of the claimed invention, rather than being impregnated, the solution may be absorbed into the fibers of the matrix, rather than filling voids between the fibers. The matrix may take the form of a disposable paper impregnated with a solution containing saline to assist in the removal of mucus. For example, the wipes may be used to clean the nose of a child, such as to care for a cold or allergies.

The absorbent matrix may be a fibrous material formed in sheets, such as single-use disposable papers. The matrix may be formed from any suitable paper having sufficient strength or appropriate chemical characteristics to not tear when wet, yet still break down once disposed. The matrix should also be stronger and denser than traditional dry facial tissues, yet still non-abrasive and flexible enough to be used on soft, curved areas of skin, such as around the nose.

For example, the matrix may be a non-woven textile having mechanically bonded fibers, such as through hydro-entanglement in which the fibers are mechanically intertwined by water jets (known as "spunlacing"). Specifically, spunlacing uses high-speed jets of water to strike fibers so that the fibers are repositioned and entangled until interlocked into a web, thereby providing matrix integrity. As a result, spunlace textiles are soft enough for hygiene applications and have better drape, conformability, wet and dry strength, absorbency and wetting relative to other non-woven textiles. A wide range of synthetic and organic or other natural fibers may be used, including, but not limited to, cotton, rayon, wood pulp, polypropylene, and polyester fibers. Such a matrix is also resistant to deterioration from chemicals and sunlight, inexpensive, and biodegradable. For example, the wipe may be a biodegradable 100 percent cotton wipe.

The matrix should have a porosity and absorbance capacity sufficient to retain the solution while having additional absorbency to remove mucus from a user. For example, the matrix should provide sufficient wet integrity to substantially maintain its ability to acquire mucus. The matrix may have a basis weight between 10 and 100 grams per square meter (gsm). An example of a suitable non-woven textile includes 45 gsm spunlace.

The thickness of the matrix may be adjusted to control the amount of liquid that may be absorbed over a given area of the matrix. The pre-moistened wipe is made by wetting the dry matrix with between 1 and 5 grams of solution per gram of matrix. For example, the dry matrix may be wetted with between 2 and 4 grams of solution per gram of matrix, or less than approximately 80 percent of the absorbent capacity of the matrix.

The solution applied to the matrix is selected to at least partially loosen, dissolve, or otherwise break down mucus so that the mucus is easier to wipe off the skin with versus without the solution. For example, the solution may loosen the mucus for easier removal relative to a dry tissue. An exemplary solution may therefore contain a loosening agent and water to dilute the loosening agent to a concentration that does not irritate the skin. The loosening agent, like an inorganic salt, may hydrate and/or dissolve, or otherwise disrupt the mucus, making it easier to remove. As well, providing the solution in an absorbent matrix, as disclosed here, allows synergism to occur between the chemical effect of the inorganic salt and the mechanical effect of the absorbent matrix on any mucus desired to be removed. As well, since the absorbent matrix should typically have unused absorbent capacity, the dissolved or disrupted mucus can be absorbed onto the matrix during a cleaning or decongesting process.

An exemplary solution includes water, sodium chloride (NaCl), glycerin, and tetrasodium ethylenediamine tetraacetic acid (EDTA). Sodium chloride may be added to the solution to assist in loosening mucus, and so in this case the sodium chloride (or other appropriate inorganic salt) is acting as a decongestant (a substance which helps to relieve congestion). In one example, the solution contains sodium chloride in a concentration in the range of 0.1-9%, such as 0.33% (i.e., 0.33 grams of sodium chloride per 100 milliliters of solution). It should be appreciated that the loosening agent may contain potassium chloride or other inorganic salts to assist in mucus removal in place of or in addition to sodium chloride.

To soften and soothe the skin, glycerin, or one of its variants, which serves as an emollient, a humectant, solvent, and/or lubricant, may be added to the solution. Other potential emollients for use are PEG-75 lanolin, PEG-40 hydrogenated castor oil, PEG-40 glyceryl cocoate, PEG-60 glyceryl stearate, or another biologically compatible emollient.

EDTA is a chelating agent that may be included to improve the stability of the cleaning solution by removing contaminants and acting as a preservative. Other suitable chelating agents may be used, such as disodium EDTA, trisodium EDTA, and/or dipotassium EDTA. Other preservatives, having an antimicrobial function, may also be added to the solution, individually or in combination. Examples of such preservatives include: iodopropynyl butylcarbamate, 2-bromo-2-nitropropane-1,3-diol, imidazolidinyl urea, DMDM hydantoin, methylchloroisothiazolinone, methylisothiazolinone, methylparaben, propylparaben, and 2-phenoxyethanol.

As noted above, the sodium chloride in the cleaning solution acts as a decongestant to remove mucus from the nasal area and free up the nasal passages for easier breathing. In some embodiments, it may be advantageous to replace, or supplement, the inorganic salt (such as sodium chloride) with a "typical" decongestant, such as pseudoephedrine. Other decongestants that could be used in this manner include oxymetazoline, xylometazoline, phenylephrine, tramazoline, ephedrine, and pseudoephedrine or any other appropriate decongestant that can be formulated in an aqueous solution.

The solution may also include one or more surfactants, such as disodium cocoamphodiacetate, to aid in removal of mucus, dirt and other substances. Alternatively, or in addition, the cleaning solution may utilize diethylhexyl sodium sulfosuccinate, ammonium cocoyl sarcosinate, ammonium cocoyl isothionate, or one of many other mild anionic surfactants.

The solution may include one or more buffering agents, such as citric acid and/or disodium phosphate, to adjust and hold steady the pH of the solution. The solution may also use as a buffer, lactic acid, phosphoric acid, potassium phosphate, disodium tartrate, disodium fumarate, sodium trimetaphospate, or another biologically appropriate buffer.

The solution may include skin care additives, such as vitamin E and/or provitamin B5, herbal supplements, such as aloe vera and chamomile, scents, and other components to improve the solution's shelf life, texture, aroma, moisturizing and healing properties, antioxidant properties and the like. For example, the solution may include various combinations and concentrations of polysorbate 20, sorbeth 30, allantoin, aloe barbadensis leaf extract, tocopheryl acetate, ascorbic acid, ascorbyl palmitate, astaxanthin, *camellia oleifera* leaf extract, *chamomilla recutita* (*matricaria*) extract, flower extract, *lavandula angustifolia* (lavender) extract, *myristica fragans* (nutmeg) extract, lauryl glucoside, panthenol, polyaminopropyl biguanide, phenoxyethanol, methyl-ethyl-propyl-butyl-isobutylparaben, citric acid, sodium citrate, and PEG-12 dimethicone.

The sheets may be stored in a sealable package configured to contain one or more sheets and substantial maintaining the moisture content in the sheet prior to use, such as during transport and storage. For example, the sheets may be stored in a plastic container, such as a bag or pouch. The package may include an opening covered by a lid through which a user may access the sheets. The sheets may be included in a package that is configured to accommodate both wet and dry sheets. For example, a package may include adjacent compartments that store wet sheets in a first compartment and dry sheets in a second compartment. In such a configuration, the wet sheets may be moistened more than a similar package of only wet sheets. For example, wet sheets that are packaged adjacent dry sheets may be impregnated with an aqueous solution in an amount greater than approximately 80 percent of the sheets absorbent capacity. FIGS. 1-4 show exemplary embodiments of containers 10 that may be used with the disclosed hydrated sheets. The container 10 may be a single-use packet 12, a wet-matrix storage box 14, or a dual- (or multi-) chambered storage container 16, 18.

In FIG. 1, the container 10 is a sachet or packet 12 made of a substantially liquid-impervious material, configured to maintain the hydration status of a stored absorbent matrix over an extended period of time. An exemplary packet would be a foil-lined pouch. Another exemplary packet may be one made of thin plastic sheeting or another appropriate synthetic material. The packet 12 may be configured to hold a single hydrated matrix sheet 20 in a folded state within the sealed edges 22 of the packet. In this way, a larger sheet can be packaged in a packet that is approximately 2 inches by 3 inches (6 cm×8 cm) along its edges 22.

Because a packet configured in the described manner may be relatively difficult to open if its edges 22 are unbroken, at least one portion of at least edge of the packet may include a notch 24 extending partially across the sealed portion of the edge. Thus, a user of the packet could grasp a textured edge 26 of the packet and initiate opening the packet at the notch 24. As an alternative, the packet could be resealable, including a Ziploc™ fastener 28 along at least portion of the packet's edge surface.

Figure 2:
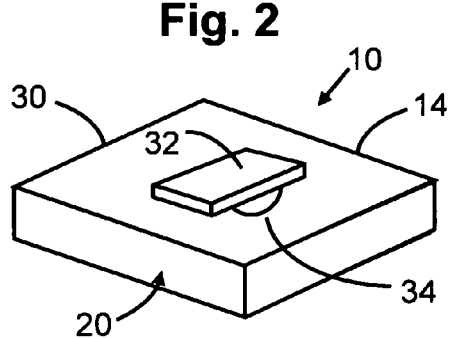
FIG. 2 is an embodiment of a container for use with a plurality of disclosed hydrated sheets.

FIG. 2 shows that the storage container for may be larger packet or box 14 configured to store a number of absorbent matrix sheets 20. In this case, the sheets may be interleaved, making them easier to withdraw from the container, one after the other. The container 14 may include a number of sturdy walls 30, or it may simply be configured as a larger version of the packet 10 (i.e. the packet 14 may have substantial depth, sufficient to store a number of sheets). Here, the storage container may include a lid 32 having a tab 34. The lid may serve to reversibly seal an opening in the container 14, allowing a single sheet to be removed for use, followed by reclosure of the container and maintenance of the hydrated status of the unused sheets.

Figure 3:
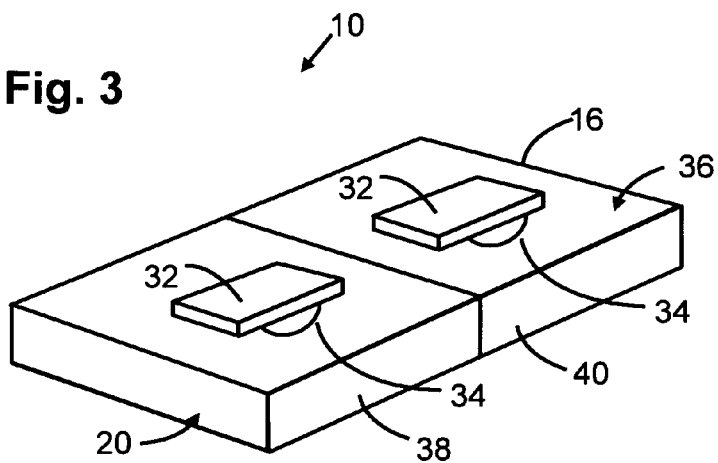
FIG. 3 is an embodiment of a multi-chambered container for use with a plurality of disclosed sheets.

FIG. 3 shows a storage container 16 having multiple compartments 38, 40 for storing absorbent matrix sheets. Alternatively, each compartment 38, 40 may store a different type of sheet. For example, in one embodiment, compartment 38 may contain hydrated matrix sheets 20 while the second compartment may contain dry matrix sheets or another type of dry sheet 36. A configuration like container 16 would allow a user to extract a hydrated matrix sheet as needed, use the sheet, and then withdraw a dry sheet for cleanup. Alternatively, the user may simply need a dry sheet (such as a Kleenex™) for blowing a child's nose, or for other use. In either case, segregation of the hydrated matrix sheets from the dry sheets allows each of them to be maintained in its most advantageous performance state (wet or dry, respectively).

Figure 4:
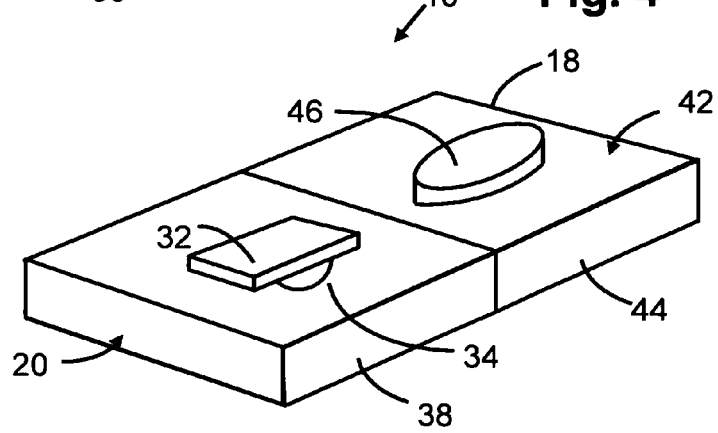
FIG. 4 is an embodiment of a multi-chambered container for use with a plurality of disclosed sheets.

Another embodiment of a container 10, shown in FIG. 4, is a multi-compartment container 18 having one compartment 38 for dry matrix sheets 20 and a second compartment 44 for cleaning solution 42. In this embodiment, the dry matrix sheets 20 and cleaning solution 42 may be separated for storage, with cleaning solution being dispensed from its compartment, onto a dry matrix sheet, as needed. For dispensing cleaning solution from its compartment, any appropriate mechanism may be used, such as a hand-actuated pump 46 or spray nozzle (if the solution is pressurized). In any case, the matrix and solution components can be stored separately, or potentially purchased separately as refills for the two compartments. Of course, though shown as having only two compartments, both this embodiment and the embodiment of FIG. 3 could be configured to have as many compartments as are necessary to store the desired number of components.

As previously discussed, the present disclosure provides a matrix impregnated with a solution containing a loosening agent. In some embodiments, the loosening agent includes an inorganic salt, such as sodium chloride. In some embodiments, the solution includes one or more of a chelating agent, a buffering agent, a surfactant, an emollient, and a fragrance. Once the matrix is impregnated with the solution, the matrix may be used to remove mucus. In some embodiments, the matrix includes a non-woven paper, which may be spunlaced and include viscose fibers.

The present disclosure further provides a nose wipe composition comprising a sheet of non-woven, absorbent, disposable material having an absorbent capacity in the range of 1 to 5 grams of liquid per 1 gram of disposable material, an aqueous solution impregnated in the sheet in an amount less than approximately 80 percent of the sheet's absorbent capacity and including sodium chloride at a concentration in the range of 1 to 9 grams per 100 milliliters of solution.

EXAMPLE 1

In line with the above discussion, a first example of an aqueous cleaning solution for use with an absorbent matrix was made according to the following composition and found to have the desired characteristics of mucus removal and skin moisturizing:

| Ingredient | Weight percent range | Function |
| --- | --- | --- |
| Sodium Chloride | 0.1-9.0 | Mucus dissolution |
| Glycerin | 0.5-7.5 | Solvent, diluent. |
| Tetrasodium EDTA | 0.05-1.5 | Metal chelator and preservative |
| Citric Acid | | pH adjustment |
| *Aloe Barbadensis* Leaf Extract | 0.01-10.0 | |
| Tocopheryl Acetate | 0.01-5.0 | |
| Polysorbate 20 | 0.2-7.5 | Surfactant |
| Iodopropynyl Butylcarbamate | 0.01-1.5 | Microbiological preservative. |
| Polyaminopropyl biguanide | | |
| *Chamomilla Recutita* Flower Extract | | |
| Lauryl glucoside | | |
| Sodium Citrate | | As needed for desired pH |
| Phenoxyethanol | | |

Additional components could be added to the formulation of Example 1 without affecting its ability to remove mucus and provide a moisturizing function. For example, the formulation of Example 1 could also include: PEG-12 dimethicone, allantoin, fragrance (as desired), and methylparaben, ethylparaben, propylparaben, or isobutylparaben. The formulation could also include panthenol, as desired.

EXAMPLE 2

Also in line with the above discussion, a second example of an aqueous cleaning solution for use with an absorbent matrix was made according to the following composition and found to have the desired characteristics of mucus removal and skin moisturizing:

| Ingredient | Weight - percent range | Function |
| --- | --- | --- |
| Sodium Chloride | 0.1-9.0 | Mucus dissolution |
| Glycerin | 0.5-7.5 | Solvent, diluent. |
| Tetrasodium EDTA | 0.05-1.5 | Metal chelator and preservative |
| Citric Acid | | pH adjustment |
| *Aloe Barbadensis* Leaf Extract | 0.01-10.0 | |
| Tocopheryl Acetate | 0.01-5.0 | |
| Polysorbate 20 | 0.2-7.5 | Surfactant |
| Iodopropynyl Butylcarbamate | 0.01-1.5 | Microbiological preservative. |
| Polyaminopropyl biguanide | | |
| *Chamomilla Recutita* Flower Extract | | |
| Lauryl glucoside | | |
| Sodium Citrate | | As needed for desired pH |
| Methylisothiazolinone | | |

As above, additional components can be added to the formulation of Example 2 without affecting its ability to remove mucus and provide a moisturizing function. For example, the formulation of Example 2 could also include: PEG-12 dimethicone, allantoin, and fragrance. Other additives are possible, according to the previous discussion.

EXAMPLE 3

Also in line with the above discussion, a third example of an aqueous cleaning solution for use with an absorbent matrix was made according to the following composition and found to have the desired characteristics of mucus removal and skin moisturizing:

| Ingredient | Weight-percent range | Function |
|---|---|---|
| Sodium Chloride | 0.1-9.0 | Mucus dissolution |
| Glycerin | 0.5-7.5 | Solvent, diluent. |
| Tetrasodium EDTA | 0.05-1.5 | Metal chelator and preservative |
| Citric Acid | | pH adjustment |
| *Aloe Barbadensis* Leaf Extract | 0.01-10.0 | |
| Tocopheryl Acetate | 0.01-5.0 | |
| Polysorbate 20 | 0.2-7.5 | Surfactant |
| Iodopropynyl Butylcarbamate | 0.01-1.5 | Microbiological preservative. |
| Polyaminopropyl biguanide | | |
| *Chamomilla Recutita* Flower Extract | | |
| Lauryl glucoside | | |
| Sodium Citrate | | As needed for desired pH |
| Allantoin | | |
| Phenoxyethanol | | |

As above, additional components can be added to the formulation of Example 3 without affecting its ability to remove mucus and provide a moisturizing function. For example, the formulation of Example 3 could also include fragrance additives as desired. Other additives are possible, according to the previous discussion.

EXAMPLE 4

For purposes of mucus removal and skin moisturizing, a range of possible and preferred concentrations of each of the above components may be included in the aqueous cleaning solution for use with an absorbent matrix. Example 4 shows typical and preferred weight-percent concentration ranges for a number of components suitable for use in the cleaning solution, with the purpose of each component noted:

| Ingredient | Weight-percent range Typical | PURPOSE |
|---|---|---|
| Sodium Chloride [Inorganic Salt] | 0.1-9.0 | Mucus dissolution. |
| Propylene Glycol [Polyhydric Alcohol] | 0.5-7.5 | Solvent, diluent. |
| Disodium EDTA [Chelating Agent] | 0.05-1.5 | Metal chelator; enhance preservatives |
| Disodium Cocoamphodiacetate [Mild Anionic Surfactant] | 0.2-7.5 | Surfactant |
| Citric Acid [pH adjustor, Buffer] | 0.1-2.5 | pH adjustment. |
| Disodium Phosphate [pH adjustor, Buffer] | 0.1-2.5 | Acid/Base buffering agent. pH adjustment. |
| *Aloe Barbadensis* Gel | 0.01-10.0 | Botanical treatment |
| *Aloe Barbadensis* Leaf Extract [Soothing Botanical] | | |
| *Aloe Barbadensis* Leaf Juice [Soothing Botanical] | | |
| Tocopheryl Acetate [Antioxidant, Free radical inhibitor] | 0.01-5.0 | Antioxidant |
| PEG-75 Lanolin [Emollient Emulsifier] | 0.2-7.5 | Emollient, lubricity, product feel |
| Polysorbate 20 [Nonionic Detergent/Solubilizer] | 0.2-7.5 | Surfactant. |
| 2-Bromo-2-Nitropropane-1,3-Diol [Microbiological Preservative] | 0.05-1.5 | Microbiological preservative. |

-continued

| Ingredient | Weight-percent range Typical | PURPOSE |
|---|---|---|
| Iodopropynyl. Butylcarbamate [Microbiological Preservative] | 0.05-1.5 | |

The disclosed embodiments and examples given above can be used in both methods of manufacture and use of a saline nose wipe. To manufacture a disclosed absorbent matrix, a user may first provide an absorbent matrix, with the matrix having an absorbent capacity of approximately 1 to 5 grams of an aqueous solution per 1 gram of matrix. The user may then impregnate into the matrix an aqueous solution having an inorganic salt in a concentration of 0.1 to 9 grams per 100 grams of solution, a preservative, and an emollient. The user may impregnate the solution into the matrix in an amount less than approximately 80 percent of the absorbent capacity of the matrix. The user may utilize any of the above disclosed solution recipes in the impregnation process. As well, though stated as "impregnation" (where the solution occupies primarily the voids of a give fabric), the user may also absorb the solution into a fabric, or use some combination of techniques to have the fabric support the solution.

A user may then use an impregnated wipe to remove mucus from around a person's nasal skin (whether the user's skin or some other person), or may use an impregnated wipe to deliver a decongestant composition to a person's nasal skin (whether the user's skin or some other person). To remove mucus, the user may first provide an absorbent matrix impregnated with an aqueous solution in an amount less than approximately 80 percent of the absorbent capacity of the matrix, with the matrix having an absorbent capacity of about 1 to 5 grams of aqueous solution per 1 gram of matrix. In this case, the solution applied typically includes an inorganic salt in a concentration of 0.1 to 9 grams per 100 grams of solution. Next, the user may dissolve and absorb mucus in or around a nose by wiping the skin around the nose with the absorbent matrix.

In using the disclosed decongestant embodiment in a decongesting process, the user will typically provide a matrix supporting a solution having a decongestant in a therapeutically effective amount. The user may then apply the decongestant in or around a nose by wiping skin around the nose with the absorbent matrix. In some cases, it may be that the use would provide an absorbent matrix supporting a solution having both cleaning and decongestant capabilities, in which case the user can remove mucus while simultaneously, or almost simultaneously, applying decongestant to the nasal area.

The concept of using the same matrix to deliver a decongestant, and to absorb and remove nasal drainage may seem counter-intuitive to some people because people are conditioned to believe fluid removal should be carried out with a highly absorbent dry matrix, and because a decongestant may take a period of time to dissolve mucus before removal. However, even if decongestant requires some time after an initial wipe to dissolve mucus, a second wipe step may be more effective in removing mucus that was dissolved or dislodged by the earlier decongestant application. Accordingly, the disclosed wipe compositions may be particularly useful and effective through multiple sequential wiping procedures.

Although the present invention has been shown and described with reference to the foregoing operational principles and preferred embodiments, it will be apparent to those skilled in the art that various changes in form and detail can be made without departing from the spirit and scope of the invention. The present invention is intended to embrace all such alternatives, modifications and variances. The subject matter of the present invention includes all novel and non-obvious combinations and subcombinations of the various elements, features, functions and/or properties disclosed herein. Inventions embodied in various combinations and subcombinations of features, functions, elements, and/or properties may be claimed through presentation of claims in a subsequent application.

We claim:

1. A method of manufacturing a matrix for removing mucus from in or around a nose comprising:
   providing an absorbent matrix of mechanically bonded fibers, wherein the matrix has an absorbent capacity of approximately 1 to 5 grams of aqueous solution per 1 gram of matrix,
   impregnating into the matrix biologically compatible alcohol-free aqueous solution comprising an inorganic salt appropriate to be applied into nasal passages in a concentration of 0.1 to 9 grams per 100 grams of solution, a preservative, and an emollient, wherein the solution is impregnated into the matrix in an amount less than approximately 80 percent of the absorbent capacity of the matrix such that the matrix has unused absorbent capacity but the amount is sufficient to apply the solution to a surface.

2. The method of claim 1 wherein the absorbent matrix is a fabric having a basis weight of approximately 10 to 100 grams per square meter.

3. The method of claim 1 wherein the absorbent matrix includes cotton.

4. The method of claim 1 wherein the inorganic salt includes one or more of: sodium chloride and potassium chloride.

5. The method of claim 1 wherein the preservative includes a chelating agent.

6. The method of claim 5 wherein the chelating agent includes one or more of: tetrasodium ethylenediamine tetraacetic acid (EDTA), disodium EDTA, trisodium EDTA, and dipotassium EDTA.

7. A disposable composition for removing mucus from in or around a nose comprising:
   an absorbent matrix of mechanically bonded fibers having an absorbent capacity of approximately 1 to 5 grams of solution per 1 gram of matrix, and
   an aqueous mucus-dissolving biologically compatible alcohol-free solution appropriate for application into nasal passages impregnated into the matrix, the amount of solution impregnated into the matrix being less than approximately 80 percent of the absorbent capacity of the matrix such that the matrix has unused absorbent capacity but the amount is sufficient to apply the solution to a surface, the solution comprising an inorganic salt in a concentration of approximately 0.1 to 9 grams per 100 grams of solution.

8. The composition of claim 7 wherein the solution further comprises an emollient, a preservative, and a surfactant.

9. The composition of claim 7 wherein the inorganic salt includes one or more of: sodium chloride and potassium chloride.

10. The composition of claim 8 wherein the emollient includes glycerin.

11. The composition of claim 8 wherein the preservative includes a chelating agent.

12. The composition of claim 11 wherein the chelating agent includes one or more of: tetrasodium ethylenediamine tetraacetic acid (EDTA), disodium EDTA, trisodium EDTA, and dipotassium EDTA.

13. The composition of claim 7 further comprising one or more of: aloe vera, lavender, chamomile, and an herbal additive.

14. The composition of claim 7 wherein the absorbent matrix is a fabric base having a basis weight of approximately 10 to 100 grams per square meter.

* * * * *

UNITED STATES PATENT AND TRADEMARK OFFICE
CERTIFICATE OF CORRECTION

PATENT NO. : 7,943,165 B2
APPLICATION NO. : 12/228426
DATED : May 17, 2011
INVENTOR(S) : Mindee K. Doney and Julienne M. Pickens It is certified that error appears in the above-identified patent and that said Letters Patent is hereby corrected as shown below:

In the Specifications:

On column 10, line 6, the words -- Microbiological Preservative -- have been omitted on Table 4 continued, under the column labeled "Purpose".

Signed and Sealed this
Thirteenth Day of August, 2013

Teresa Stanek Rea
*Acting Director of the United States Patent and Trademark Office*